United States Patent [19]

Tatnall

[11] Patent Number: 5,500,368
[45] Date of Patent: Mar. 19, 1996

[54] FINELY DIVIDED ANTHRAQUINONE FORMULATIONS AS INHIBITORS OF SULFIDE PRODUCTION FROM SULFATE-REDUCING BACTERIA

[75] Inventor: Robert E. Tatnall, Chadds Ford, Pa.

[73] Assignee: Bio-Technical Resources, Manitowoc, Wis.

[21] Appl. No.: 327,331

[22] Filed: Oct. 21, 1994

Related U.S. Application Data

[63] Continuation-in-part of Ser. No. 122,614, Sep. 21, 1993, abandoned, which is a continuation-in-part of Ser. No. 955,623, Oct. 2, 1992, abandoned.

[51] Int. Cl.$^6$ .................................. B09B 3/00; C12N 1/00
[52] U.S. Cl. ................ 435/262; 435/243; 435/266; 435/281
[58] Field of Search ...................... 435/29, 32, 34, 435/184, 281, 262, 243

[56] References Cited

U.S. PATENT DOCUMENTS 5,385,842  1/1995  Weimer et al. ..................... 435/262

FOREIGN PATENT DOCUMENTS

WO91/15954  10/1991  WIPO ..................... A01N 35/06

OTHER PUBLICATIONS

S. Okabe, et al., Factors Affecting Microbial Sulfate Reduction by Desulfovibrio . . . Biotech. and Bioeng. 40:725, 1992.

*Primary Examiner*—John W. Rollins

[57] ABSTRACT

A method of inhibit sulfide production in a media containing sulfate-reducing bacteria is disclosed. The method comprises adding particles of a finely divided sulfide production-inhibiting anthraquinone to the medium. The particles have a particle size of 0.1 to 2.5 microns, preferably 2 to 0.1 microns.

21 Claims, 2 Drawing Sheets

FINELY DIVIDED ANTHRAQUINONE FORMULATIONS AS INHIBITORS OF SULFIDE PRODUCTION FROM SULFATE-REDUCING BACTERIA

REFERENCE TO RELATED APPLICATION

This application is a continuation-in-part of application Ser. No. 08/122,614, filed Sep. 21, 1993, now abandoned, incorporated herein by reference, which is a continuation-in-part of application Ser. No. 07/955,623 filed Oct. 2, 1992, now abandoned.

FIELD OF THE INVENTION

The invention relates to a method for inhibiting sulfide production by sulfate-reducing bacteria comprising adding finely divided sulfate production-inhibiting anthraquinones to media that contain sulfate-reducing bacteria.

BACKGROUND OF THE INVENTION

As described in PCT WO91/15954, incorporated herein by reference, and in Wiemer, U.S. Pat. No. 5,385,842, many anthraquinones and their anthraquinol and tetrahydroxyanthraquinone derivatives inhibit sulfide production from sulfate-reducing bacteria. Thus, they potentially useful for treating industrial media in which biological sulfide generation is a problem. The term sulfate-reducer encompasses a broad spectrum of organisms across both eubacterial and archaebacterial branches of bacterial phylogeny. Many sulfate-reducing bacteria are known, particularly those of the genera Desulfovibrio, Desulfotomaculum, Desulfobacter, Desulfobulbus, Desulfococcus, Desulfonema, Desulfosarcina and Thermodesulfobacterium.

There are currently about 130 different industrial biocide products registered with the U.S. Environmental Protection Agency. Although many have demonstrated effectiveness against sulfate-reducing bacteria, none are specific for these bacteria. These biocides can not be used in situations in which it is desired to inhibit sulfate-reducing bacteria, but not adversely affect other bacteria, as in, for example, municipal sewage treatment plants.

SUMMARY OF THE INVENTION

The invention is a method for inhibiting sulfide production in a medium containing sulfate-reducing bacteria, the method comprising adding to the medium, in a quantity sufficient to inhibit sulfide production, particles of a sulfide production-inhibiting anthraquinone, wherein the particles have an average particle size of about 0.1–2.5 microns.

DETAILED DESCRIPTION OF THE INVENTION

Figure 1:
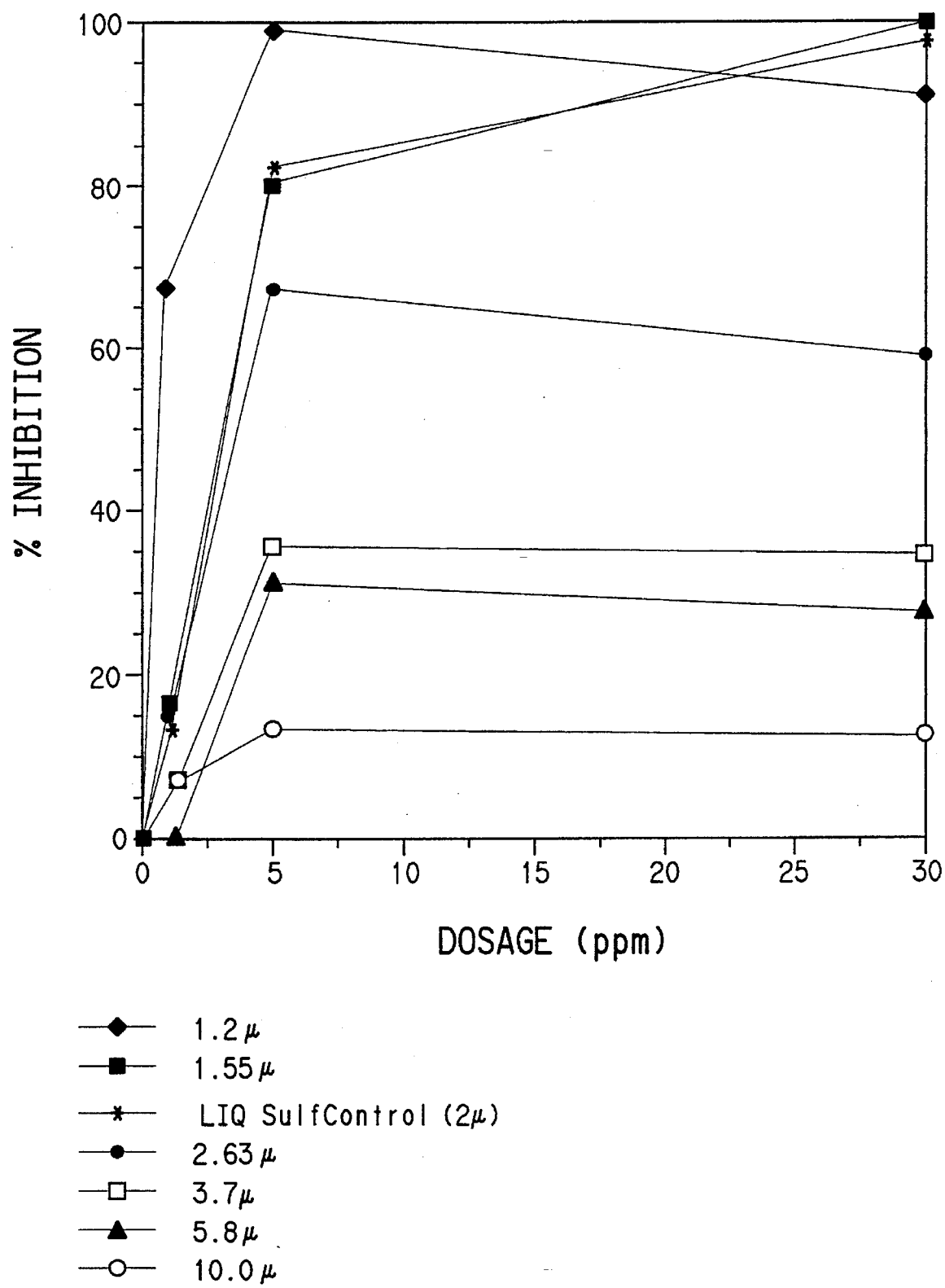
FIG. 1 shows the effect of the size of the 9,10-anthraquinone particles in inhibiting the growth of sulfate-reducing bacteria after 24 hr.

The invention is a method to inhibit sulfide production by sulfate-reducing bacteria comprising adding a finely divided sulfide production-inhibiting anthraquinones to an aqueous medium containing the sulfate-reducing bacteria. The term "finely divided" means that the anthraquinone in the composition has an average particle size of less than 2.51 $\mu$ and preferably less than 2.0 $\mu$. As a practical matter the minimum particle size is about 0.1 $\mu$. As the average particle size is decreased within the "finely divided" range the activity of the anthraquinone increases.

The activity of the anthraquinones is a function of particle size and not available surface area. An anthraquinone particles having an average particle size of 2.0 $\mu$ used at a concentration of 5 ppm provides satisfactory inhibition of growth of sulfate-reducing bacteria. Particles of the same anthraquinone that have an average particle size of 3.7 $\mu$ used at a concentration of 30 ppm do not provide satisfactory inhabitation of growth of sulfate reducing bacteria. This difference in effectiveness due to particle size is readily apparent upon initial application of the anthraquinone but is even more pronounced a short time after application of the anthraquinone when the effectiveness of the larger particle size anthraquinones is effectively completely lost.

The compositions are add to the medium containing the sulfate-reducing bacteria in a quantity sufficient to inhibit sulfide production. As little as 1 ppm in the aqueous medium gives significant inhibition for many uses. In the preferred method the concentration of active anthraquinone in the medium is at least 5 ppm, desirably 5–50 ppm. Greater concentrations, such as up to 100 ppm, of course can be used, but in most cases with little advantage so long as the "finely divided" particle size requirement is met.

The term "anthraquinone(s)", as used in this application, means anthraquinones, the corresponding anthraquinol derivatives, the corresponding tetrahydroanthraquinones, the corresponding octahydroanthraquinones, and the reduced derivatives thereof. The activity of an anthraquinone can be predicted from analysis of the substituents present. This is discussed in detail in WO91/15954 and in Wiemer, U.S. Pat. No. 5,385,842. The preferred anthraquinones are 9,10-anthraquinone, 1,8-dihydroxyanthraquinone, 1-chloroanthraquinone, 2-chloroanthraquinone, 2-chloroanthraquinone-3-carboxylic acid, 1,5-dihydroxyanthraquinone, 1-aminoanthraquinone, 2-aminoanthraquinone, 2,6-dihydroxyanthraquinone, 1,2-dihydroxyanthraquinone, 1-hydroxyanthraquinone and 1,5-dichloroanthraquinone. A more preferred anthraquinone is 9,10-anthraquinone, commonly referred to as anthraquinone.

Many of the active anthraquinones, including those listed above, are commercially available. The preparation of anthraquinone and anthraquinol derivatives from anthraquinones is well known to those skilled in the art.

Sulfide production by a number of different sulfate-reducing bacteria is inhibited. When 3 ppm of an inhibitory anthraquinone is added to a growing culture of Desulfovibrio sp., growth and sulfide formation immediately cease. This cessation typically lasts for several days after which growth resumes. This effect has been demonstrated with several different species of Desulfovibrio in pure culture.

The compositions comprise at least one finely divided, relatively non-soluble hydrophobic anthraquinone. Although the composition may be in the form of a suspension in water or a water-miscible carrier, the preferred compositions are dry, free-flowing particles such as a wettable powder.

Because of the hydrophobic nature and low water solubility of the anthraquinone (<10 ppm for most compounds), the preferred compositions also contain a surfactant, or wetting agent. The surfactant can be applied by any of a variety of techniques. In the case of a normally solid surfactant, the surfactant and the anthraquinone can be dry blended, preferably prior to the milling step. In the case of a normally liquid surfactant the surfactant can be sprayed onto the anthraquinone followed by mixing such as tumbling to ensure that an intimate well dispersed mixture is obtained. Alternatively a liquid solution of the surfactant can be sprayed on the anthraquinone and the anthraquinone further mixed.

The choice of surfactant is not critical. Any of the commercially available surfactants that are inert to the anthraquinone and other composition ingredients and are compatible with the use environment are suitable. Typical of such surfactants are nonionic, cationic and anionic with the nonionic surfactants being preferred. These include Triton® X-100, a nonionic octylphenoxypolyethoxyethanol, available from Rohm & Haas; Poly-Tergent® SLF18, poly(oxyethylene)-poly(oxypropylene)-monohexylether; mono-octylether; mono-decylether, available from Olin Corp.; Morwet® D-425, an anionic sodium salt of condensed naphthalene sulfonate, available from Witco Chemical Co.; Stepsperse® DF-500, an anionic blend of lignin sulfonates, available from Stephan Co.; Stepwet® DF-90, an anionic linear alkylbenzene sulfonate, available from Stephan Co.; Stepsperse® DF-100, an anionic/nonionic blend including lignin sulfonate, available from Stephan Co.; Stepflow® 41, an anionic lignin sulfonate, available from Stephan Co.; and Stepflow® 24, a nonionic nonylphenolethoxylate, available from Stephan Co.

The surfactant is present in the dry compositions, for example a wettable powder, in an amount to enable the anthraquinone particles to be quickly wetted and thoroughly dispersed in the aqueous bacteria use locus. Quantities in the range of 2–15%, based on the weight of the anthraquinone, are generally preferred.

The sulfate-reducing bacteria are typically present in an aqueous medium, one in which the liquid phase consists essentially of water. The preferred aqueous media do not comprise added organic solvents.

It has been found that the redox potential of the culture affects the potency of the anthraquinone. Compounds are most effective when added to a culture in early exponential growth where some sulfide has already been produced thus rendering the medium more reduced than uninoculated medium. However, compounds still show some inhibition when added to oxidized medium which is subsequently inoculated. It has been shown that use of a reducing agent can enhance the strength of the inhibition even when the inhibitor is added concurrently with the inoculum. This aspect would suggest that the compounds are most effective under anaerobic, reduced conditions as would be found in, for example a sewage treatment anaerobic digestor, or in another respect the compounds may be thought of as being activated by the end-product of the sulfate-reducer which is sulfide.

The compositions sometimes may advantageously contain a reducing agent. Any reducing agent that eliminates oxidative tendencies of the medium, and that is inert to the composition ingredients and compatible with the use environment can be used. The preferable amount of reducing agent is that which will introduce about 2–4 mM/L in the medium. A useful reducing agent is sodium sulfide.

The bulk anthraquinones are normally obtained as particles or granules of comparatively large average particle size, as dry powders or slurries. To prepare the compositions, the anthraquinones are comminuted to the required finely divided particle size, which can be ascertained using conventional means such as a Coulter counter or a laser particle analyzer. Any means for particle size reduction may be used, such as ball milling, sand milling, pin milling, air milling, and wet milling with an agitator. In the preferred technique, dry bulk anthraquinone is dry milled to the critical particle size, and then admixed with the other ingredients, such as, if present, surfactant and reducing agent. If desired, these other ingredients may be introduced during the particle size reduction. Generally the finely divided anthraquinone is used in the form of aqueous suspension containing 10–60 wt % of an anthraquinone.

The preferred compositions contain: 10–60 wt % of the anthraquinone, 0.5–2.5 wt % of a nonylphenolethoxylate, 0.1–1.5 wt % of sodium lignosulfonate, 0.1–1.0 wt % of calcium lignosulfonate, 0.05–2.0 wt % of a xanthan gum and the remainder water. In a more preferred aspect, the aqueous suspension additionally comprises: 0.005–0.3 wt % 1,2-benzothiazolin-3-one, 0.1–1.0 wt % polydimethylsiloxane, and 1.0–10 wt % propylene glycol. In an even more preferred aspect, the aqueous suspension contains: 45–55 wt % 9,10-anthraquinone, 0.5–1.5 wt %, 1 wt % 10 mole nonylphenolethoxylate and 0.2–0.5 wt % sodium lignosulfonate, 0.1–0.3 wt % calcium lignosulfonate, 0.1–0.5 wt % magnesium aluminum silicate, 0.05–0.5 wt % xanthan gum, and the balance water. Additionally the most preferred aqueous suspension contains 0.05–0.3 wt % 1,2-benzothiazolin-3-one, 0.1–0.4 wt % polydimethylsiloxane, and 2–5 wt % propylene glycol.

INDUSTRIAL APPLICABILITY

The method can be used to treat industrial media in which biological sulfide generation is a problem. It can be used to prevent the souring of oil wells with hydrogen sulfide and to prevent contamination of surface operations such as pipelines and storage tanks with hydrogen sulfide. It can also be used for odor and corrosion control in the pulp and paper industry. The anthraquinones are relatively benign environmentally and many are relatively specific for inhibiting sulfide generation. Hence the method is useful in situations in which broad-spectrum biocides cannot be used, such as municipal sewage treatment.

The advantageous properties of the invention can be observed by reference to the following examples which illustrate, but do not limit, the invention.

EXAMPLES

Example 1

9,10-Anthraquinone, obtained from Lancaster Synthesis Ltd, was blended with surfactants, silica and clay as reported in Table 1 below. The blended ingredients were then ground to various average particle sizes either by dry grinding in a laboratory air mill or by wet grinding as an aqueous slurry using a Netzsch Molinex Agitator mill. Average particle size was determined with a Leeds & Northrup Microtrac SPA laser instrument.

TABLE 1

| Sample ID | Formula | Weight % | Grinding Method | Avg. Particle Size (microns) |
|---|---|---|---|---|
| A | Mobay 9,10-anthraquinone (AQ) | 79.9 | Wet | 3.49 |
|  | Stepwet ® DF-90 wetting agent | 1.5 | | |
|  | Stepsperse ® DF-500 dispersant | 7 | | |
|  | Stepsperse ® DF-100 dispersant | 6 | | |
|  | PPG Hi-Sil ® 233 hydrated amorphous silica | 0.5 | | |
|  | barden clay | 5 | | |
|  | Eastman Kodak SWS-211 antifoam | 0.1 | | |
| B | Same as "A" but without the DF-90; AQ was | 81.4% | Wet | 2.86 |
| C | Mobay AQ | 79 | Dry | 2.73 |
|  | Stepwet ® DF-90 | 1.5 | | |
|  | Stepsperse ® DF-500 | 7 | | |
|  | Stepsperse ® DF-100 | 6 | | |
|  | Hi-Sil ® 233 | 1 | | |
|  | barden clay | 5.5 | | |
| D | Lancaster Synthesis AQ | 90 | Dry | 1.84 |
|  | Stepwet ® DF-90 | 0.5 | | |
|  | Stepsperse ® DF-500 | 6 | | |
|  | Stepsperse ® DF-100 | 3 | | |
|  | Hi-Sil ® 233 | 0.5 | | |
| E | same as "B" | | Wet | 1.52 |
| F | same at "B" | | Wet | 0.95 |
| G | Mobay AQ | 0.1 | — | Acetone Solution |

These preparations were then dispersed in water to produce a concentrated suspension of 9,10-anthraquinone particles of known concentration (except for "G", which was used directly as prepared).

Serum bottles of 60 mL capacity were each filled to the 50 mL level with Postgate's "B" medium designed for growing sulfate reducing bacteria. The Postgate's medium was first deaerated, and then transferred to the bottles under nitrogen. The bottles were capped with elastomeric septum closures, and then autoclaved.

Into two of these bottles was injected a pure culture of *Desulfovibrio desulfuricans* strain G100A, as isolated by the DuPont Co. These cells were allowed to grow and proliferate overnight at 30° C. to produce a bacteria enrichment suspension.

To determine the relative effectiveness of the various 9,10-anthraquinone preparations as sulfide inhibitors, additional serum bottles containing Postgate's B medium were first inoculated with the above cell inoculum, 3 mL/bottle. Two of these were then set aside as untreated controls. The remainder were additionally inoculated with known quantities of 9,10-anthraquinone from the above preparations. All bottles were then shaken to homogenize contents and assayed for total hydrogen sulfide using the standard methylene blue colorimetric method and Hach, Co. reagents. This number was recorded as the "starting" level of sulfide.

The bottles were then incubated at 30° C. for about 30 hr, then reshaken and again assayed for total sulfide. The bottles treated with 1 ppm 9,10-anthraquinone were compared with the untreated controls, and percent inhibition determined. Results are shown in Table 2.

TABLE 2

| Compound Code | Avg. Part. (microns) | Percent Inhibition |
|---|---|---|
| A | 3.49 | 12 |
| B | 2.86 | 15 |
| C | 2.73 | 20 |
| D | 1.84 | 39 |
| E | 1.52 | 46 |
| F | 0.95 | 66 |
| G | — | 75 |

The effectiveness of the acetone solution would normally be greater than shown here—more on the order of 95% to 98% inhibition at the 1 ppm dose rate (based on many tests by the method described). The lower level seen here indicates that the incubation time was too long, so that the few "uninhibited" bacteria had begun to grow significantly and produce hydrogen sulfide. Nonetheless, these numbers are still useful to indicate "relative" effectiveness of the various 9,10-anthraquinone preparations. The conclusion drawn is that inhibition effectiveness is a function of anthraquinone particle size—i.e. the smaller the particle the better it's performance as a sulfide inhibitor.

Example 2

9,10-Anthraquinone from ICI Americas, Inc., was blended as per the following formula:

9,10-Anthraquinone - 79% w/w

Stepwet® DF-90 - 2%

Stepsperse® DF-100 - 6%

Stepsperse® DF-500- 7%

Hi-Sil® 233-1% barden clay- 5%

This powder compound was then ground in a laboratory air mill to produce various average particle sizes. These compounds were compared in a biological test identical to that described in Example 1, and the results compared to no treatment and to an acetone solution of 9,10-anthraquinone. Results are shown in Table 3.

TABLE 3

| Avg. Particle Size (microns) | Percent Inhibition |
|---|---|
| 5.66 | 0 |
| 3.61 | 14 |
| 2.13 | 35 |
| 1.34 | 82 |
| 1.33 | 94 |
| Acetone treatment | 92 |

A strong correlation between particle size and inhibition was observed. Particles near or below about 2 microns perform much better than particles in the 3–6 micron range. These tests involved single data points with each compound, and there is some inherent imprecision in the methods.

Example 3

A pure strain of *Desulfovibrio gigas* was grown overnight in a lactate medium and the cells harvested by centrifugation, then resuspended in Hepes buffer at pH 7. The cell suspension was then recentrifuged, the supernatant discarded, and the cells suspended in a solution of 50 mM Hepes buffer, 50 mM sodium lactate and 50 mM sodium sulfate. This cell suspension was placed in evacuated glass tubes and then gassed with hydrogen to reduce the medium and to provide a hydrogen-rich atmosphere in the tubes. The Hepes/lactate/sulfate medium was chosen because it would support cell respiration (i.e. enzyme reactions such as sulfate reduction), but would not, in a short test, support significant cell metabolism and growth.

The tubes were treated with the same 9,10-anthraquinone formulation described in Example 2. Some tubes were left untreated as controls. After 3 hr at 30° C., sulfide levels in the liquid medium in the tubes were measured, and compared with the control tubes to determine percent inhibition. Results at the 0.5 ppm 9,10-anthraquinone level are shown in Table 4.

TABLE 4

| Avg. Particle Size (microns) | Percent Inhibition |
| --- | --- |
| 5.66 | 0 |
| 3.61 | 8 |
| 2.13 | 76 |
| 1.34 | 95 |
| <0.1 | 97 |

Example 4

This example illustrates inhibition by 9,10-anthraquinone ball milled to different average particle sizes. The suspensions contained 51.5 wt. % 9,10-anthraquinone, 1 wt. % 10 mole nonylphenolethoxylate, 0.3 wt. % sodium lignosulfonate, 0.2 wt. % calcium lignosulfonate, 0.3 wt. % magnesium aluminum silicate, 0.1 wt. % 1,2 benzothiazolin-3-one, 0.2 wt. % polydimethylsiloxane, 2.5 wt. % propylene glycol and the remainder water. The suspensions were tested as described in Example 1. Results are shown in FIG. 1.

Figure 2:
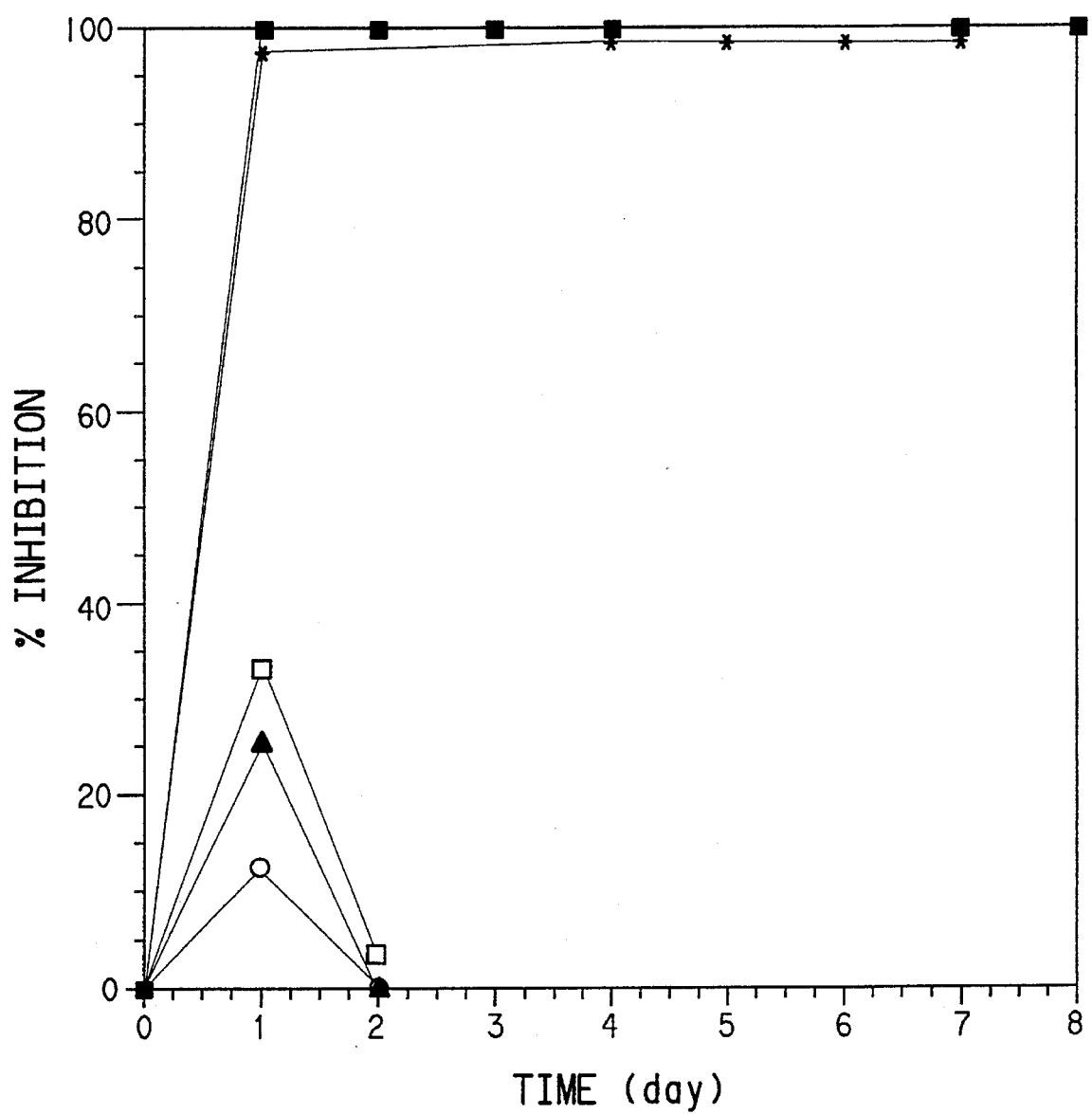
FIG. 2 shows the effect of the size of the 9,10-anthraquinone particles in inhibiting the growth of sulfate-reducing bacteria over a period of several days.

As can be seen from FIG. 1, after 24 hr the 1.2 micron particle size 9,10-anthraquinone is nearly 100% effective at the 5 ppm dosage level and slightly less effective at the 30 ppm dosage level. The 1.55 and 2 micron particle size materials are about 80% effective at the 5 ppm dosage level and are about 100% effective at the 30 ppm dosage level. The 2.63 micron particle size material is moderately effective, but not as effective as the smaller particle size materials. The larger particle size materials, i.e. 3.7 micron, 5.8 micron and 10 micron, are poor inhibitors. FIG. 2 shows the effectiveness of 9,10-anthraquinone of various particle sizes at the 30 ppm dosage level over a period of several days. As can be seen from FIG. 2, the 1.55 micron and 2 micron average particle size materials retain their effectiveness over a period of at least 7–8 days while the 3.7 micron and larger particle size materials lose essentially all of their effectiveness after only two days.

What is claimed is:

1. A method for inhibiting sulfide production in a medium containing sulfate-reducing bacteria, the method comprising adding to the medium, in a quantity sufficient to inhibit sulfide production, particles of a sulfide production-inhibiting anthraquinone, wherein the particles have an average particle size of about 0.1–2.5 microns.

2. The method of claim 1 in which the anthraquinone is 9,10-anthraquinone.

3. The method of claim 1 in which addition produces an anthraquinone concentration of from 1 to 100 parts per million in the medium.

4. The method of claim 3 in which the average particle size is 0.1–2 microns.

5. The method of claim 1 in which the anthraquinone is selected from the group consisting of 9,10-anthraquinone, 1,8-dihydroxyanthraquinone, 1-chloroanthraquinone, 2-chloroanthraquinone-3-carboxylic acid, 1,5-dihydroxyanthraquinone, 1-aminoanthraquinone, 2-aminoanthraquinone, 2,6-dihydroxyanthraquinone, 1,2-dihydroxyanthraquinone, 1-hydroxyanthraquinone and 1,5-dichloroanthraquinone.

6. The method of claim 5 in which addition produces an anthraquinone concentration of from 1 to 100 parts per million in the medium.

7. The method of claim 6 in which the medium is sewage.

8. The method of claim 6 in which the average particle size is 0.1–2 microns.

9. The method of claim 7 in which the anthraquinone is 9,10-anthraquinone.

10. The method of claim 8 in which addition produces an anthraquinone concentration of from 5 to 50 parts per million in the medium.

11. The method of claim 1 in which the anthraquinone particles are coated with 2 to 15 weight percent of a surfactant.

12. The method of claim 11 in which the anthraquinone is selected from the group consisting of 9,10-anthraquinone, 1,8-dihydroxyanthraquinone, 1-chloroanthraquinone, 2-chloroanthraquinone-3-carboxylic acid, 1,5-dihydroxyanthraquinone, 1-aminoanthraquinone, 2-aminoanthraquinone, 2,6-dihydroxyanthraquinone, 1,2-dihydroxyanthraquinone, 1-hydroxyanthraquinone and 1,5-dichloroanthraquinone.

13. The method of claim 12 in which addition produces an anthraquinone concentration of from 1 to 100 parts per million in the medium.

14. The method of claim 13 in which the anthraquinone is 9,10-anthraquinone.

15. The method of claim 13 in which the average particle size is 0.1–2 microns.

16. The method of claim 11 in which the surfactant is nonionic.

17. The method of claim 16 in which addition produces an anthraquinone concentration of from 1 to 100 parts per million in the medium.

18. The method of claim 17 in which the anthraquinone is 9,10-anthraquinone.

19. The method of claim 18 in which the medium is sewage.

20. The method of claim 1 in which the sulfide production-inhibiting anthraquinone is added to the medium containing sulfate-reducing bacteria as an aqueous suspension containing 10–60 weight % of the anthraquinone.

21. The method of claim 20 in which the sulfide production-inhibiting anthraquinone is 9,10-anthraquinone.

* * * * *